(12) United States Patent
Chez

(10) Patent No.: US 7,709,213 B2
(45) Date of Patent: May 4, 2010

(54) METHOD FOR DIAGNOSING A PERVASIVE DEVELOPMENTAL DISORDER

(76) Inventor: Michael Chez, 201 Cuddington Ct., Granite Bay, CA (US) 95746

( * ) Notice: Subject to any disclaimer, the term of this patent is extended or adjusted under 35 U.S.C. 154(b) by 0 days.

(21) Appl. No.: 11/759,568

(22) Filed: Jun. 7, 2007

(65) Prior Publication Data

US 2008/0305551 A1 Dec. 11, 2008

(51) Int. Cl.
*G01N 33/96* (2006.01)
*G01N 33/53* (2006.01)

(52) U.S. Cl. ....................................................... 435/7.1
(58) Field of Classification Search ........................ None
See application file for complete search history.

(56) References Cited

U.S. PATENT DOCUMENTS 7,252,957 B2   8/2007   Vajdani

OTHER PUBLICATIONS

Sperner-Unterweger. Immunological aetiology of major psychiatric disorders: evidence and therapeutic implications. Drugs. 2005;65(11):1493-520.*
Levitt et al. The genetic and neurobiologic compass points toward common signaling dysfunctions in autism spectrum disorders. J Clin Invest. Apr. 2009;119(4):747-54. Epub Apr. 1, 2009.*
Gupta, S., "Immunological treatments for autism," J Autism Dev Disord., Oct. 2000; 30(5):475-9.
Plioplys, AV., "Intravenous immunoglobulin treatment in autism," J Autism Dev Disord., Feb. 2000 ; 30(1): 73-4.
Chez, M., et al., "Clinical Inflammatory Markers in CSF of Autistic Children with Regression," Annals of Neurology, Sep. 2006, vol. 60 (suppl 3), p. S68-S69.
Chez, M. G., et al., "Elevation of Tumor Necrosis Factor-Alpha in Cerebrospinal Fluid of Autistic Children," Pediatric Neurology, Jun. 2007, pp. 361-365, vol. 36 No. 6.
Chez, M. G., et al., "Frequency of eplieptiform EEG abnormalities in a sequential screening of autistic patients with no known clinical epilepsy from 1996 to 2005," Epilepsy & Behavior, 2006.
Kubisch, C., et al., "Autosomal Recessive Rippling Muscle Disease with Homozygous CAV3 Mutations," American Neurological Association, 2005, pp. 303-304, vol. 57, No. 2.
Nelson, K. B., et al., "Neuropeptides and Neurotrophins in Neonatal Blood of Children with Autism or Mental Retardation," Annals of Neurology, 2001, pp. 597-606, vol. 49, No. 5.
Vargas, D. L., et al., "Neuroglial Activation and Neuroinflammation in the Brain of Patients with Autism," American Neurological Association, 2004, pp. 67-81, vol. 57, No. 1.
Vezzani, A., "Brain Inflammation in Epilepsy: Experimental and Clinical Evidence," Epilepsia, 2005, pp. 1724-1743, vol. 46, No. 11.
Zimmerman, A. W., et al., "Cerebrospinal Fluid and Serum Markers of Inflammation in Autism," Pediatric Neurology, 2005, pp. 195-201, vol. 33 No. 3.

Wilner, A. N., "Elevated Tumor Necrosis Factor Found In Cerebrospinal Fluid of Autistic Children," Neurology News, 2007.
Connolly AM, et al., "Serum Autoantibodies to Brain in Landau-Kleffner Variant, Autism and Other Neurologic Disorders," J. Pediatr 199; 134:607-13.
Connolly AM, et al., "Brain-Derived Neurotrophic Factor and Autoantibodies to Neural Antigeus in Sera of Children with Autistic Spectrum Disorders, Landau-Kleffner Syndrome, and Epilepsy," Biol. Psychiatry, 2006; 59:354-63.
Todd RD, et al., "Antibrain Antibodies in Infantile Autism," Biol. Psychol., 1988; 23:644-7.
Singh VK, et al., "Antibodies to Myelin Basic Protein in Children with Autistic Behavior," Brain Behav Immun., 1993; 7:97-103.
Pickering M, et al., "Actions of TNF-a on Glutaminergic Synaptic Transmission in the Central Nervous System," Exp. Physiol. 2005; 90:663-70.
Attallah AM, et al. "Immunodetection of a Hepatitis C Virus (HCV) Antigen and Th1/Th2 Cytokines in Cerebrospinal Fluid of Meningitis Patients," J Immunoassay Immunochem 2005; 25:313-20.
Baraczka K, et al., "Investigation of Cytokine (Tumor Necrosis Factor-Alpha, Interleukin-6, Interleukin-10) Conecntrations in the Cerebrospinal Fluid of Female Patients with Multiple Sclerosis and Systemic Lupus Erythematosus," Eur J Neurol. 2004; 11:37-42.
Monno L, et al. "Angarano G. Reduced Concentrations of HIV-RNA and TNF-a Coexist in CSF of AIDS Patients with Progressive Multifocal Leukoencephalopathy," J Neurol Neurosurg. Psychiatry, 1999; 67:369-73.
Shiozaki T, et al. Cerebrospinal Fluid Concentrations of Anti-Inflammatory Mediators in Early-Phase Severe Traumatic Brain Injury, Shock 2005; 23:406-10.
Sjogren M, et al., Increased Intrathecal Inflammatory Activity in Frontotemporal Dementia: Pathophysiological Implications,: J Neurol. Neurosurg. Psychiatry 2004; 75:1107-11.
Vila N, et al. "Proinflammatory Cytokines and Early Neurological Worsening in Ischemic Stroke," Stroke 2000; 31:2325-9.
Kanner L., et al., "Autistic Disturbances of Affective Contact," Nervous Child, 1943; 2:217-50.

* cited by examiner

*Primary Examiner*—Daniel E. Kolker
*Assistant Examiner*—Gregory S Emch
(74) *Attorney, Agent, or Firm*—Cahn & Samuels LLP

(57) ABSTRACT

A method for diagnosing a pervasive developmental disorder, such as autism, comprising obtaining a sample of cerebrospinal fluid from a subject; obtaining a sample of serum from a subject; testing the cerebrospinal fluid of the subject for a concentration of TNF-α; testing the serum of the subject for a concentration of TNF-α; and positively diagnosing a pervasive developmental disorder when the concentration ratio of TNF-α in the cerebrospinal fluid of the subject to TNF-α in the serum of the subject exceeds approximately 2:1 over normal control concentrations.

19 Claims, No Drawings

METHOD FOR DIAGNOSING A PERVASIVE DEVELOPMENTAL DISORDER

BACKGROUND OF THE INVENTION

1. Field of the Invention

The present invention relates in general to a method for diagnosing a pervasive developmental disorder, for example, autism.

2. Background Art

Since the first clinical descriptions of autism in the 1940s, there has been no definite etiology or pathological finding leading to a cure or reversal of the condition. Recent reports suggest that there may be a combination of environmental or perhaps in utero risk factors, possible autoimmune risk factors, and perhaps localized inflammation of central nervous system neuroglia pointing to a compartmentalized central nervous system inflammatory response in at least some patients with autism.

Although no specific cell count elevation or direct central nervous system antibodies have been found, some recent studies of cytokines in the central nervous system may implicate an isolated response separate from the peripheral immune system.

These studies have not addressed direct neuroglial or innate central nervous system immune responses. The reports of elevated cytokines support possible increased tumor necrosis factor alpha (TNF-α) levels, in that interleukin-6 and elevated levels of TNF-receptor I antibodies have been reported in the cerebrospinal fluid of autistic patients. The role of TNF-α as a neuromodulating agent has been described in brain development as well, and it may play a role in neurons and neuroglial cells modulating glutaminergic transmission. Excessive glutamate excitotoxic effects acting on NMDA receptors could occur in the presence of excess TNF-α. This occurrence can lead to effects on microglial activation as well as other cytokines, such as nuclear factor-kappa-beta (NF-Kβ), among others. Such changes have also been seen in models of inflammation inducing epileptic activity in which neuroglial inflammation has caused epileptic spikes. Because of the high frequency of epileptic spikes seen in some subgroups of autistic children, and given that similar inflammatory mechanisms may play a role in spike formation, this finding may be more than a coincidence.

Vargas D L, et al. Neuroglial activation and neuroinflammation in the brain of patients with autism, Ann Neural 2005; 57:304 and Zimmerman A, et al. Cerebrospinal fluid and serum markers of inflammation in autism, Pediatr Neurol 2005; 35:195-201, disclose measuring cytokine profiles. However, neither article measures TNF-α, much less comparing the levels of TNF-α in cerebrospinal fluid and serum at the same time.

However, to the best of Applicant's knowledge, there are currently no known biological early diagnostic markers to identify at risk patients for a pervasive developmental disorder or to monitor treatment targets.

SUMMARY OF THE INVENTION

It is an object of the present invention to provide a method for positively diagnosing a pervasive developmental disorder (PDD), which may allow early diagnosis in infancy or the first 2 years of life, and may allow early medical treatment to possibly alter the course of a disease, for example, autism.

It is another object of the present invention to use a TNF-α ratio as a key marker for abnormal central nervous system cytokine inflammation causing autistic disease.

Yet another object of the present invention is directed to monitoring and designing therapy for PDDs by showing an improvement in an elevated, abnormal ratio to a more normal TNF-α ratio.

Another object of the present invention is directed to diagnosing, for example, some catastrophic epilepsies utilizing the same ratio analysis.

The above objects are satisfied by a method for diagnosing a pervasive developmental disorder, such as autism, comprising obtaining a sample of cerebrospinal fluid (CSF) from a subject; obtaining a sample of serum from a subject; testing the cerebrospinal fluid of the subject for a concentration of TNF-α; testing the serum of the subject for a concentration of TNF-α; and positively diagnosing a pervasive developmental disorder when the concentration ratio of TNF-α in the cerebrospinal fluid of the subject to TNF-α in the serum of the subject exceeds approximately 2:1 over normal control concentrations.

In at least one embodiment, obtaining samples of cerebrospinal fluid and serum from a subject occur substantially simultaneously.

In at least one embodiment, positively diagnosing a PDD occurs when the concentration ratio of TNF-α (CSF) to TNF-α (serum) of a subject exceeds approximately at least one of 5:1, 10:1, 20:1, 50:1, 100:1, 250:1, or 500:1 over normal control concentrations.

In at least one embodiment, obtaining samples of CSF and serum from a subject occurs in a subject less than at least one of 84, 72, 60, 48, 36, 24, or 12 months old.

It will be understood that regardless of its ordinary meaning the term "normal control concentrations" will be defined as concentrations that are within a reasonable range for a subject (e.g., human patient) without a pervasive developmental disorder.

As used herein "substantially", "generally", "relatively", "approximately", and "about" are relative modifiers intended to indicate permissible variation from the characteristic so modified. It is not intended to be limited to the absolute value or characteristic which it modifies but rather approaching or approximating such a physical or functional characteristic.

References to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

DETAILED DESCRIPTION OF THE INVENTION

In accordance with the present invention, a method for diagnosing a pervasive developmental disorder (PDD), such as autism, is provided which comprises obtaining a sample of cerebrospinal fluid from a subject; obtaining a sample of serum from a subject; testing the cerebrospinal fluid (CSF) of the subject for a concentration of tumor necrosis factor alpha (TNF-α); and testing the serum of the subject for a concentration of TNF-α. In the case of an adolescent, e.g., a child 12 years or younger, a pervasive developmental disorder is positively diagnosed when the concentration ratio of TNF-α in the cerebrospinal fluid to TNF-α in the serum exceeds approximately 2:1 over normal control concentrations.

It will be understood that obtaining a sample of CSF from a subject, obtaining a sample of serum from a subject, testing the CSF of the subject for a concentration of TNF-α, and testing the serum of the subject for a concentration of TNF-α, are procedures and tests known by medical professionals having ordinary skill in the art.

In at least one embodiment of the present invention, obtaining samples of CSF and serum from the subject occur substantially simultaneously, for example, the samples are generally drawn at the same time.

In at least one embodiment of the present invention, positively diagnosing a PDD occurs when the concentration ratio of TNF-α in the CSF of the subject to TNF-α in the serum of the subject exceeds at least one of approximately 2:1, 5:1, 10:1, 20:1, 50:1, 100:1, 250:1, or 500:1 over normal control concentrations.

In at least one embodiment of the present invention, obtaining samples of CSF and serum from the subject occurs in a subject less than at least one of 84, 72, 60, 48, 36, 24, or 12 months old. Such early diagnosis may allow for reversal or at least enhanced therapy relative to conventional methods.

It will be understood that the present invention may also be helpful in diagnosing some catastrophic epilepsies.

In at least one embodiment, the present invention may be useful as a way to monitor and design therapy for at least one condition by showing an improvement in an elevated abnormal TNF-α (CSF) to TNF-α (serum) ratio to a normal ratio.

According to the present invention, the TNF-α (CSF) to TNF-α (serum) ratios are significantly elevated in autistic patients compared with patients in other known disease states and with control groups in the medical literature. There is no apparent correlation in the elevation of TNF-α levels between the CSF and serum of autistic patients, indicating that the effects on the levels within the CSF and serum are independent of the other.

This finding contrasts with the correlation suggested from review of previous studies, where changes in one TNF-α level generally corresponded with changes in the other TNF-α level, thus suggesting systemic inflammation, not isolated in the central nervous system. The finding according to the present invention suggests that, even ignoring the numerical difference between the levels of TNF-α in CSF and serum, there is a mechanism possibly unique to autism in which changes of TNF-α levels in the CSF may be independent of changes in the serum. Such a mechanism suggests a unique and isolated CNS response. Whether this response is genetic or environmentally induced is unclear, and whether it is due to an error in neurodevelopment or to immune system response is also unknown.

According to the present invention, there is an observed trend suggesting the possibility that a child's ratio of TNF-α in CSF and serum is a potential marker for the pathological process involved in autistic regression. This marker may reflect neuroglial and immune mechanisms found in the central nervous system different from typical infectious, autoimmune, or traumatic mechanisms previously described in the literature (in predominantly adult populations). The TNF-α ratio offers unique and specific therapeutic targets for treatment. This value of relative elevation may allow a biological marker to identify children at risk, and also allow for design of disease-altering treatment through lowering of TNF-α levels. Theoretically, if introduced early, such treatment could alter the course of the disease development and could allow tracking clinically. TNF-α levels in the CSF may be an early marker, allowing clinical diagnosis of autism, even before obvious clinical features become evident.

EXAMPLES

Example 1

Table 1 shows data for TNF-α in CSF and TNF-α in serum of patients (children) with autism. Four of the patients had not been previously treated for autism.

TABLE 1

TNF-α levels in autistic patients (pg/mL)

| Patient | Treated | CSF | Serum | CSF-serum ratio |
|---|---|---|---|---|
| 1 | No | 124 | 1.6 | 77.5 |
| 2 | No | 140 | 2.0 | 70.0 |
| 3 | No | 181 | 8.2 | 22.1 |
| 4 | No | 16 | 2.1 | 7.6 |
| 5 | Yes | 12 | 1.7 | 7.1 |
| 6 | Yes | 13 | 1.3 | 10.0 |
| 7 | Yes | 11 | 1.3 | 8.5 |
| 8 | Yes | 4 | 2.3 | 1.7 |
| Averages | Not Treated | 115.25 | 3.47 | 33.17 |
|  | Treated | 10.00 | 1.65 | 6.06 |
|  | Overall | 62.63 | 2.56 | 24.44 |

TNF-α is elevated in the cerebrospinal fluid of children with autism and regression, even in cases previously treated with known immunosuppressive agents. The fact that these children showed consistently higher ratios of CSF to serum TNF-α suggests a compartmentalized local reaction in the central nervous system. This finding differs from previous literature as discussed below.

Based upon a review of other known conditions that affect the central nervous system, such as stroke, infection, multiple sclerosis, systemic lupus, traumatic brain injury, and human immunodeficiency virus or acquired immunodeficiency syndrome (HIV/AIDS) infection, the cerebrospinal fluid and serum levels of TNF-α were approximately 1:1 in both test and control groups, as shown in Tables 2-3. Of 37 reviewed articles addressing tumor necrosis factor in humans, 25 measured TNF-α levels in the cerebrospinal fluid or serum, and 6 of these studies allowed for direct comparison of the two between test groups and control groups, wherein N represents the number of patients.

TABLE 2

TNF-α levels in other conditions (pg/mL)

| Authors | Diagnosis | CSF | N | Serum | N |
|---|---|---|---|---|---|
| Attallah & Ibrahim, 2004 | Meningitis | 123.3 | 21 | 88.6 | 21 |
| Baraczka et al., 2004 | MS | 2.4 | 50 | 1.32 | 50 |
| Baraczka et al., 2004 | Systemic Lupus Erythematosus | 1.8 | 50 | 2.63 | 50 |
| Monno et al., 1999 | HIV[1] | 6.0 | 13 | 22 | 11 |
| Monno et al., 1999 | HIV[2] | 11.3 | 9 | 50.1 | 8 |
| Monno et al., 1999 | HIV[3] | 17.8 | 25 | 38.3 | 22 |
| Shiozaki et al., 2005 | Traumatic Brain Injury | 16.6 | 18 | 5.1 | 18 |
| Sjögren et al., 2004 | Dementia | 0.6 | 15 | 3.4 | 19 |
| Vila et al., 2000 | Stroke | 22.8 | 33 | 21.1 | 83 |
| Weighted means | | 19.16 | | 19.33 | |

[1] w/ progressive multifocal leukoencephalopathy
[2] w/ HIV-1 leukoencephalopathy
[3] w/ opportunistic infections

TABLE 3

TNF-α levels in control conditions (pg/mL)

| Authors | Diagnosis | CSF | N | Serum | N |
|---|---|---|---|---|---|
| Attallah & Ibrahim, 2004 | Control | 63.42 | 19 | 65.3 | 19 |
| Baraczka et al., 2004 | Control | 0.42 | 50 | 1.66 | 50 |
| Monno et al., 1999 | Control | 4.2 | 8 | 36 | 11 |
| Shiozaki et al., 2005 | Control | 18.4 | 17 | 5 | 17 |
| Sjögren et al., 2004 | Control | 0 | 5 | normal | — |
| Vila et al., 2000 | Control | 11.1 | 48 | 15.1 | 148 |
| Weighted Means | | 14.18 | | 16.49 | |

TNF-α CSF-to-serum ratios ranged from 0.18 to 3.25 (mean=1.04, S.D.=1.01) for test groups and 0.12 to 3.68 (mean=1.15, S.D.=1.46) for control groups. There were no indications that these values differed significantly from the expected 1:1 ratio (t=0.266, P=0.795), nor were there indications that the CSF-to-serum ratios differed significantly between the test groups and the control groups (t=−0.168, P=0.869).

Weighted analyses of these studies suggested that there were no statistically significant differences overall in TNF-α levels between test groups and control groups in serum (t=1.638, P=0.102) or cerebrospinal fluid (t=1.758, P=0.080), nor between serum and CSF in test groups (t=0.066, P=0.947) or control groups (t=1.117, P=0.265).

A ranked correlation analysis suggested relations between TNF-α levels in the cerebrospinal fluid and the serum of patients in the test groups (r=0.717, P=0.030) but not the control groups (r=0.500, P=0.391). The largest ratio between TNF-α levels in CSF and serum was found in a study of patients with traumatic brain injury, in which both the test group (traumatic brain injury with extracranial injury) and the control group (traumatic brain injury without extracranial injury) showed elevated ratios.

As shown in Table 4, the overall TNF-α CSF-to-serum ratios were 0.99 for patients of Table 2 and 0.86 for controls of Table 3. In contrast, the overall TNF-α CSF-to-serum ratios for the autistic patients of Table 1 were significantly higher.

TABLE 4

Comparison of TNF-α in CSF and serum levels and ratios

| | CSF Levels (pg/mL) | Serum Levels (pg/mL) | Ratios |
|---|---|---|---|
| Autism (Table 1) | | | |
| Not Treated | 115.25 | 3.47 | 33.17 |
| Treated | 10.00 | 1.65 | 6.06 |
| Overall | 62.63 | 2.56 | 24.44 |
| Other Studies | | | |
| Test Groups (Table 2) | 19.16 | 19.33 | 0.99 |
| Control Groups (Table 3) | 14.18 | 16.49 | 0.86 |

Example 2

TNF-α Study

I. Patients

Ten male pediatric patients meeting DSM-IV-TR criteria for autism with a history of regression in language and eye contact between 15 and 24 months of age were given the option of having a lumbar puncture performed under a general anesthetic while undergoing such sedation for neuroimaging studies such as a diagnostic scheduled magnetic resonance imaging study of their brains. All families gave written and verbal consent for the procedures. In addition, one male patient (age 2.8 years) with Lennox-Gastant syndrome and speech delay had a lumbar puncture as part of his epilepsy evaluation and had only spinal fluid levels of TNF-α measured, providing a spontaneous single alternative case to compare whether the CSF TNF-α would be elevated in a young severely epileptic child with language delay as well.

Of the 10 patients, 4 had been previously treated for presumed autoimmune issues clinically with prednisone, thalidomide, or carnosine and turmeric supplements. These particular patients also had treatment with valproic acid for abnormal sleep electroencephalographic patterns with frequent sleep-activated central-temporal spikes but not a continuous spike-wave in sleep pattern or Landau-Kleffner diagnosis. Patient characteristics are given in Table 5.

TABLE 5

Characteristics of autistic patients in TNF-α study

| Patient | Sex | Age, years | Age of Regression, months | 24-hr EEG Baseline at Initial Visit | Prior Immunosuppressive Therapy | Current Medications |
|---|---|---|---|---|---|---|
| 1 | M | 9.5 | 18 | Abnormal sleep temporal-central spike-wave R > L. | Pulse dose prednisone and thalidomide in past; turmeric at time of CSF study | Memantine, valproic acid, risperdal, focalin |
| 2 | M | 6.0 | 24 | Centrotemporal spike-wave activity in sleep R > L. | Pulse dose prednisone, IVIG in past; turmeric at time of CSF study | Valproic acid, memantine, carnitine |
| 3 | M | 4.5 | 15 | Sleep right temporal spikes | None | Valproic acid |
| 4 | M | 4.5 | 15 | Sleep right and left temporal spikes | None | Valproic acid |
| 5 | M | 8.3 | 18 | Secondary generalized polyspikes from temporal lobes in sleep | Pulse dose prednisone in past; turmeric at time of CSF study | Valproic acid, memantine, adderall |
| 6 | M | 6.7 | 15 | Generalized polyspikes in sleep | Brief prednisone in past; turmeric at time of CSF study | Valproic acid, memantine, carnitine |
| 7 | M | 2.5 | 15 | Bilateral temporal and secondary generalized spikes in sleep | None | Valproic acid |
| 8 | M | 4.5 | 18 | Mild left temporal slowing in sleep | None | None |

TABLE 5-continued

Characteristics of autistic patients in TNF-α study

| Patient | Sex | Age, years | Age of Regression, months | 24-hr EEG Baseline at Initial Visit | Prior Immunosuppressive Therapy | Current Medications |
| --- | --- | --- | --- | --- | --- | --- |
| 9 | M | 2.5 | 15 | Normal | None | None |
| 10 | M | 9.7 | 24 | Normal | None | None |

CSF = Cerebrospinal fluid
EEG = Electroencephalogram
IVIG = Intravenous immunoglobulin
R > L = Greater activity over the right versus left side II. Methods The procedure was elective and was done to rule out a degenerative process. The patients had routine clinical CSF studies performed including cell count for red and white blood cells, total protein, and glucose levels. The calculation of production of immunoglobulin synthesis and oligoclonal bands, myelin basic protein, and glutamate levels were also performed. In addition, levels of TNF-α were simultaneously drawn from serum and CSF. The CSF samples were frozen and analyzed by Inter Science Institute (Inglewood, Calif.) using a quantitative sandwich enzyme immunoassay technique with a monoclonal antibody specific for TNF-α. The TNF-α levels in CSF and serum of patients were analyzed and ratios were calculated. The ratios were analyzed with a paired-samples r test, and relation trends were examined with correlation analyses.

III. Results

All patients had normal red and white cell counts in their CSF. They also had normal protein, glucose, and glutamate levels. The CSF showed no elevation of myelin basic protein, an absence of oligoclonal bands, and no evidence of immunoglobulin synthesis. TNF-α levels are reported in Table 6.

TABLE 6

TNF-α levels in serum and cerebrospinal fluid

| Patient | Autoimmune Treatment | CSF (pg/mL) | Serum (pg/mL) | CSF/Serum Ratio |
| --- | --- | --- | --- | --- |
| 1 | No | 124 | 1.6 | 77.5 |
| 2 | No | 140 | 2.0 | 70.0 |
| 3 | No | 181 | 8.2 | 22.1 |
| 4 | No | 16 | 2.1 | 7.6 |
| 5 | No | 155 | 2.7 | 57.4 |
| 6 | No | 385 | 1.4 | 275 |
| 7 | Yes | 12 | 1.7 | 7.1 |
| 8 | Yes | 13 | 1.3 | 10.0 |
| 9 | Yes | 11 | 1.3 | 8.5 |
| 10 | Yes | 4 | 2.3 | 1.7 |
| | Mean | 104.1 | 2.5 | 53.7 |
| | S.D. | 121.3 | 2.3 | |

All but one patient had normal (<8.2 pg/mL) serum levels of TNF-α, ranging from 1.3 to 8.2 pg/mL. The CSF levels of TNF-α ranged from 4 to 385 pg/mL and were higher particularly in the patients who were naïve to prior immunomodulatory therapies. An established reference range for TNF-α levels in CSF is not available.

The overall ratio of the average CSF-to-serum levels for TNF-α was 53.7, with ratios for individual patients ranging from 1.7 to 275. Paired sample analysis suggests a significant difference between serum and cerebrospinal fluid (t=2.384, P=0.049), and independent t tests indicate significantly higher TNF-α levels in the cerebrospinal fluid of untreated patients in comparison with treated patients (t=2.986, P=0.024) (patients 1-6 and 7-10, respectively).

The CSF-to-serum ratios for the untreated and treated patients were 55.6 and 6.3, respectively, and the TNF-α levels in the serum were found to not be significantly different between the two groups. Overall, there is no correlation evident in TNF-α levels between samples taken from the cerebrospinal fluid and serum (r=0.311, P=0.453).

Elevation of cerebrospinal fluid levels of TNF-α was significantly higher than concurrent serum levels of TNF-α in all of the patients studied. The ratio averaged 53.7:1. This ratio is significantly higher than the elevations reported for other pathological states for which cerebrospinal fluid and serum TNF-α levels have been simultaneously measured.

The single patient with Lennox-Gastaut syndrome had cerebrospinal fluid levels of TNF-α of 2 pg/mL, clearly below the levels seen in the autistic patients.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A method for diagnosing a pervasive developmental disorder, comprising:
   obtaining a sample of cerebrospinal fluid from a subject;
   obtaining a sample of serum from a subject;
   testing the cerebrospinal fluid of the subject for a concentration of TNF-α;
   testing the serum of the subject for a concentration of TNF-α; and
   positively diagnosing a pervasive developmental disorder when the concentration ratio of TNF-α in the cerebrospinal fluid of the subject to TNF-α in the serum of the subject exceeds 2:1 over normal control concentrations.

2. The method according to claim 1, wherein said obtaining samples of cerebrospinal fluid and serum from the subject occur simultaneously.

3. The method according to claim 1, wherein said positively diagnosing the pervasive developmental disorder occurs when the concentration ratio of TNF-α in the cerebrospinal fluid of the subject to TNF-α in the serum of the subject exceeds 10:1 over normal control concentrations.

4. The method according to claim 1, wherein said positively diagnosing the pervasive developmental disorder occurs when the concentration ratio of TNF-α in the cerebrospinal fluid of the subject to TNF-α in the serum of the subject exceeds 50:1 over normal control concentrations.

5. The method according to claim 1, wherein said positively diagnosing the pervasive developmental occurs when the concentration ratio of TNF-α in the cerebrospinal fluid of the subject to TNF-α in the serum of the subject exceeds 250:1 over normal control concentrations.

6. The method according to claim 1, said positively diagnosing the pervasive developmental disorder occurs when the concentration ratio of TNF-α in the cerebrospinal fluid of the subject to TNF-α in the serum of the subject exceeds 500:1 over normal control concentrations.

7. The method according to claim 1, wherein said obtaining samples of cerebrospinal fluid and serum from the subject occurs in a subject less than 84 months old.

8. The method according to claim 1, wherein said obtaining samples of cerebrospinal fluid and serum from the subject occurs in a subject less than 48 months old.

9. The method according to claim 1, wherein the step of obtaining samples of cerebrospinal fluid and serum from the subject occurs in a subject less than 24 months old.

10. The method according to claim 1, wherein the step of obtaining samples of cerebrospinal fluid and serum from the subject occurs in a subject less than 12 months old.

11. The method according to claim 1, wherein the pervasive development disorder comprises autism.

12. The method according to claim 1, wherein the subject is human.

13. The method according to claim 12, wherein the subject is male.

14. The method according to claim 1, wherein the subject has not had prior immunosuppressive therapy.

15. The method according to claim 14, wherein said positively diagnosing the pervasive developmental disorder occurs when the concentration ratio of TNF-α in the cerebrospinal fluid of the subject to TNF-α in the serum of the subject exceeds 55:1 over normal control concentrations.

16. The method according to claim 1, wherein the subject has had prior immunosuppressive therapy.

17. The method according to claim 16, wherein said positively diagnosing the pervasive developmental disorder occurs when the concentration ratio of TNF-α in the cerebrospinal fluid of the subject to TNF-α in the serum of the subject exceeds 6:1 over normal control concentrations.

18. A method for diagnosing autism, comprising:
    obtaining a sample of cerebrospinal fluid from a child less than about 84 months old;
    obtaining a sample of serum from the child, wherein said obtaining samples of cerebrospinal fluid and serum from the child occur simultaneously;
    testing the cerebrospinal fluid of the child for a concentration of TNF-α;
    testing the serum of the child for a concentration of TNF-α; and
    positively diagnosing autism when the concentration ratio of TNF-α in the cerebrospinal fluid to TNF-α in the serum exceeds 2:1 over the concentration ratio of TNF-α in the cerebrospinal fluid of a subject to TNF-α in the serum of a child without autism.

19. A method for monitoring a therapy for pervasive developmental disorder, comprising:
    obtaining a sample of cerebrospinal fluid from a subject;
    obtaining a sample of serum from a subject;
    testing the cerebrospinal fluid of the subject for a concentration of TNF-α;
    testing the serum of the subject for a concentration of TNF-α; and
    monitoring the concentration ratio of TNF-α in the cerebrospinal fluid of the subject to TNF-α in the serum of the subject.

* * * * *